United States Patent
Chaki et al.

(10) Patent No.: US 8,975,456 B2
(45) Date of Patent: Mar. 10, 2015

(54) METHOD FOR PURIFYING 2,3,3,3-TETRAFLUOROPROPENE

(75) Inventors: Takehiro Chaki, Settsu (JP); Kazuhiro Takahashi, Settsu (JP); Yoshinori Tanaka, Settsu (JP); Hitoshi Yoshimi, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 321 days.

(21) Appl. No.: 13/505,520

(22) PCT Filed: Nov. 9, 2010

(86) PCT No.: PCT/JP2010/070258
§ 371 (c)(1),
(2), (4) Date: May 2, 2012

(87) PCT Pub. No.: WO2011/059078
PCT Pub. Date: May 19, 2011

(65) Prior Publication Data
US 2012/0222448 A1 Sep. 6, 2012

Related U.S. Application Data

(60) Provisional application No. 61/272,845, filed on Nov. 10, 2009, provisional application No. 61/376,341, filed on Aug. 24, 2010.

(51) Int. Cl.
*C07C 17/25* (2006.01)
*C07C 17/383* (2006.01)
(52) U.S. Cl.
CPC .................................. *C07C 17/383* (2013.01)
USPC .............................. 570/177; 203/57; 510/408
(58) Field of Classification Search
CPC ..................................................... C07C 17/383
USPC .............................. 510/408; 570/177; 203/57
See application file for complete search history.

(56) References Cited

U.S. PATENT DOCUMENTS

| 2,996,555 A | 8/1961 | Rausch |
| 2008/0011678 A1* | 1/2008 | Knapp ........................... 210/634 |

(Continued)

FOREIGN PATENT DOCUMENTS

| CN | 101541715 | 9/2009 |
| WO | WO 2008/002499 | 1/2008 |

(Continued)

OTHER PUBLICATIONS

International Search Report issued Jan. 28, 2011 in International (PCT) Application No. PCT/JP2010/070258, of which the present application is the national stage.

(Continued)

*Primary Examiner* — Gregory Webb
(74) *Attorney, Agent, or Firm* — Wenderoth, Lind & Ponack, L.L.P.

(57) ABSTRACT

The present invention provides a method for purifying HFO-1234yf, comprising the steps of (1) cooling a liquid mixture containing HFO-1234yf and HF to separate the mixture into a upper liquid phase having a high concentration of HF and a lower liquid phase having a high concentration of 2,3,3,3-tetrafluoropropene; and (2) subjecting the lower liquid phase obtained in step (1) to a distillation operation to withdraw a mixture containing HFO-1234yf and HF from a top of a distillation column, thereby obtaining substantially HF-free HFO-1234yf from a bottom of the distillation column. According to the present invention, HF and HFO-1234yf contained in a mixture containing HF and HFO-1234yf can be separated under simple and economically advantageous conditions.

14 Claims, 5 Drawing Sheets

(56) References Cited

U.S. PATENT DOCUMENTS

2009/0118555 A1* 5/2009 Wang et al. .................. 570/227
2009/0240090 A1* 9/2009 Merkel et al. ................ 570/160
2009/0287027 A1* 11/2009 Merkel et al. ................ 570/164

FOREIGN PATENT DOCUMENTS

| WO | WO 2008/008519 | 1/2008 |
| WO | WO 2008/024508 | 2/2008 |
| WO | WO 2009/003084 | 12/2008 |
| WO | WO 2009/105512 | 8/2009 |
| WO | WO 2009/105517 | 8/2009 |

OTHER PUBLICATIONS

Written Opinion issued Jan. 28, 2011 in International (PCT) Application No. PCT/JP2010/070258, of which the present application is the national stage.

* cited by examiner

METHOD FOR PURIFYING 2,3,3,3-TETRAFLUOROPROPENE

This application claims the benefit of U.S. Provisional Application No. 61/272,845, filed Nov. 10, 2009, and U.S. Provisional Application No. 61/376,341, filed Aug. 24, 2010.

TECHNICAL FIELD

The present invention relates to a method for purifying 2,3,3,3-tetrafluoropropene from a mixture containing 2,3,3,3-tetrafluoropropene and hydrogen fluoride.

BACKGROUND ART 2,3,3,3-tetrafluoropropene (HFO-1234yf) represented by chemical formula: $CF_3CF=CH_2$ is considered to be promising as a refrigerant for car air-conditioners because its global warming potential (GWP) is low.

In regard to a method for producing HFO-1234yf, there are various known methods such as a method in which $CCl_3CF_2CH_3$ as a starting material is reacted with hydrogen fluoride (HF) having an amount exceeding the stoichiometric amount (PTL 1); a method in which fluorocarbon represented by $CF_3CFHCFH_2$ is subjected to dehydrofluorination (PTL 2); etc.

In these methods, outflow from the reaction vessel is a mixture containing not only a desired product, i.e., HFO-1234yf, but also HF in an amount equal to or greater than the equimolar amount of HFO-1234yf. Accordingly, HF needs to be removed from the mixture containing HFO-1234yf and HF in order to purify and commercialize HFO-1234yf. As a method therefor, there is a known method in which a mixture containing HFO-1234yf and HF is treated with water or an alkali solution to adsorb HF. However, this method requires a large amount of water or alkali solution, resulting in the discharge of a large amount of industrial wastewater. It is thus undesirable in terms of environmental protection and production costs.

Further, as another method for removing HF, there is a method in which a mixture containing HFO-1234yf and HF is reacted with $H_2SO_4$ so as to collect HF as hydrofluoric-sulfuric acid. However, in this method, the produced hydrofluoric-sulfuric acid has strong corrosivity, and thus materials for the equipment used must be highly corrosion resistant. This leads to an increase in production costs.

Further, in the case of the above method for removing HF, high technology is required to reuse the removed HF. This leads to an increase in production costs not only when HF is discarded but also when the collected HF is recycled.

As a method for solving these problems, for example, PTL 3 discloses a method for separating HFO-1234yf from HF contained in a mixture of HFO-1234yf and HF by using, as an extractant, a compound having a high mutual solubility with HFO-1234yf. However, in this method, a step of separating HFO-1234yf and the extractant is necessary after removing HF. This contributes to an increase in production costs. Further, use of an extractant creates a risk of contamination by impurities that are unnecessary for the process, and thus adds an increased burden in terms of process control and quality control.

Further, for example, PTL 4 discloses a method for obtaining HFO-1234yf from the bottom of a distillation column by distilling a mixture of HFO-1234yf and HF, and withdrawing an azeotrope-like mixture of HFO-1234yf and HF from the top of the distillation column. However, this method requires withdrawal of a large amount of HFO-1234yf along with HF from the top of the column, and thus the size of the distillation column is relatively large. Also, when a method for recycling an azeotropic mixture is employed, the size of the equipment used for the process is relatively large because the amount of a mixture of HFO-1234yf and HF to be circulated is large. These are the factors that contribute to an increase in equipment costs and the running costs of the process.

CITATION LIST

Patent Literature

PTL 1: U.S. Pat. No. 2,996,555
PTL 2: WO 2008/002499A1
PTL 3: WO 2008/008519
PTL 4: WO 2009/105512 A1

SUMMARY OF INVENTION

Technical Problem

The present invention is made in light of the above-described technical problems. A main object of the present invention is to provide a method for separating HF from HFO-1234yf contained in a mixture containing HF and HFO-1234yf under simple and economically advantageous conditions.

Solution to Problem

The present inventors conducted intensive studies in an attempt to achieve the above-described object. As a result, they discovered a conventionally unknown phenomenon, that is, when a liquid mixture containing HF and HFO-1234yf as main components is cooled, the liquid mixture is separated into an upper liquid phase having a high concentration of HF and a lower liquid phase having a high concentration of HFO-1234yf. The present inventors also found that distillation of the lower liquid phase having a high concentration of HFO-1234yf, which is obtained by liquid-liquid separation using the above method, allows withdrawal of a mixture containing HFO-1234yf and HF from the top of a distillation column, and thereby HF contained in the lower liquid phase is removed, thus obtaining substantially HF-free HFO-1234yf from the bottom of the column. It was found that particularly when the mixture containing HFO-1234yf and HF to be withdrawn from the top of the distillation column is an azeotropic or azeotrope-like mixture of HFO-1234yf and HF, HF contained in the lower liquid phase can be separated by withdrawing a small amount of the mixture, and substantially HF-free HFO-1234yf can be efficiently obtained from the bottom of the column. It was also found that when the mixture containing HFO-1234yf and HF to be withdrawn from the top of the distillation column is a non-azeotropic mixture, impurities having a boiling point between the boiling point of an azeotropic mixture and the boiling point of HFO-1234yf, among impurities contained in the lower liquid phase, can be separated from the lower liquid phase together with HF contained therein by the distillation operation, and thus substantially HF-free HFO-1234yf having a reduced amount of impurities can be efficiently obtained from the bottom of the column. The present invention has been completed as a result of further studies based on such findings.

Specifically, the present invention provides a method for purifying 2,3,3,3-tetrafluoropropene from a mixture of 2,3,3,3-tetrafluoropropene and hydrogen fluoride as described below.

1. A method for purifying 2,3,3,3-tetrafluoropropene comprising the steps of:
   (1) cooling a liquid mixture containing 2,3,3,3-tetrafluoropropene and hydrogen fluoride to separate the liquid mixture into an upper liquid phase having a high hydrogen fluoride concentration and a lower liquid phase having a high 2,3,3,3-tetrafluoropropene concentration;
   (2) subjecting the lower liquid phase obtained in step (1) to a distillation operation and withdrawing a mixture containing 2,3,3,3-tetrafluoropropene and hydrogen fluoride from a top of a distillation column, thereby obtaining 2,3,3,3-tetrafluoropropene that does not substantially contain hydrogen fluoride from a bottom of the distillation column.
2. The method according to Item 1, wherein the mixture containing 2,3,3,3-tetrafluoropropene and hydrogen fluoride withdrawn from the top of the distillation column in step (2) is an azeotropic or azeotrope-like mixture.
3. The method according to Item 1, wherein the mixture containing 2,3,3,3-tetrafluoropropene and hydrogen fluoride withdrawn from the top of the distillation column in step (2) is a non-azeotropic mixture.
4. The method according to any one of Items 1 to 3, wherein the temperature to cool the liquid mixture containing 2,3,3,3-tetrafluoropropene and hydrogen fluoride in step (1) is −5° C. or below.
5. The method according to any one of Items 1 to 4, wherein cooling in step (1) is performed on the liquid mixture containing 2,3,3,3-tetrafluoropropene and hydrogen fluoride to which the mixture containing 2,3,3,3-tetrafluoropropene and hydrogen fluoride withdrawn from the top of the distillation column is added.
6. The method according to any one of Items 1 to 5, wherein the liquid mixture containing 2,3,3,3-tetrafluoropropene and hydrogen fluoride to be cooled in step (1) further contains 2-chloro-3,3,3-trifluoropropene.
7. The method for purifying 2,3,3,3-tetrafluoropropene according to Item 6, further comprising a step of subjecting the column bottom product obtained in step (2) to a distillation operation to remove 2-chloro-3,3,3-trifluoropropene.

Treatment Targets of the Present Invention

The treatment target of the present invention is a liquid mixture containing 2,3,3,3-tetrafluoropropene (HFO-1234yf) represented by chemical formula: $CF_3CF=CH_2$ and hydrogen fluoride represented by chemical formula: $HF$. The types of liquid mixtures are not particularly limited. Examples of treatment targets include a product obtained by dehydrofluorination operation of fluorocarbon, a product obtained by fluorination operation of chlorofluorohydrocarbon, etc. The treatment targets may also include a product obtained by combining the above-described operations, and a product obtained by distilling the above-described products.

The ratio between HFO-1234yf and HF in the treatment target is not particularly limited. Any mixture, regardless of the ratio, can be separated into a hydrogen fluoride-rich upper liquid phase and an HFO-1234yf-rich lower liquid phase by adjusting the cooling temperature in the below-described liquid-liquid separation step.

Further, a mixture containing HFO-1234yf and HF may contain other components insofar as they do not interfere with the effects of the below-described liquid-liquid separation step and distillation step. For example, when producing HFO-1234yf by fluorination of 2-chloro-3,3,3-trifluoropropene (HCFO-1233xf) represented by $CF_3CCl=CH_2$, a mixture that contains not only HFO-1234yf as a product but also raw materials such as HCFO-1233xf and HF is obtained. Such a mixture containing HFO-1234yf, HCFO-1233xf, and HF can also be a treatment target of the present invention.

Other examples of treatment targets of the present invention include mixtures that contain the following:
1,1,2,3-tetrachloropropene (HCFO-1230xa) represented by $CH_2ClCCl=CCl_2$; 2,3,3-trichloro-3-fluoropropene (HCFO-1231xf) represented by $CCl_2FCCl=CH_2$; 1,2,3-trichloro-1-fluoropropene (E,Z—HCFO-1231xb) represented by $CH_2ClCCl=CClF$;
1,1,2-trichloro-3-fluoropropene (HCFO-1231xa) represented by $CH_2FCCl=CCl_2$; 1,3,3-trichloro-3-fluoropropene (E,Z—HCFO-1231zd) represented by $CCl_2FCH=CHCl$;
2,3-dichloro-3,3-difluoropropene (HCFO-1232xf) represented by $CClF_2CCl=CH_2$; 2,3-dichloro-1,1-difluoropropene (HCFO-1232xc) represented by $CH_2ClCCl=CF_2$;
1,1,1,2,3-pentachloropropane (HCC-240db) represented by $CCl_3CHClCH_2Cl$; 1,1,2,3-tetrachloro-1-fluoropropane (HCFC-241db) represented by $CCl_2FCHClCH_2Cl$;
1,2,3-trichloro-1,1-difluoropropane (HCFC-242dc) represented by $CClF_2CHClH_2Cl$; 1,2-dichloro-3,3,3-trifluoropropane (HCFC-243db) represented by $CF_3CHClCH_2Cl$;
2-chloro-1,1,1,2-tetrafluoropropane (HCFC-244bb) represented by $CF_3CClFCH_3$; 1,1,1,2,3-pentafluoropropane (HFC-245eb) represented by $CF_3CHFCH_2F$; 1,1,1,2,2-pentafluoropropane (HFC-245cb) represented by $CF_3CF_2CH_3$; trifluoroethane represented by $CF_3CH_3$; 3,3,3-trifluoropropyne;
1,2,3,3,3-pentafluoropropene (E,Z—HFO-1225ye) represented by $CF_3CF=CHF$; 1,1,3,3,3-pentafluoropropene (HFO-1225zc) represented by $CF_3CH=CF_2$; 1,3,3,3-tetrafluoropropene (E,Z—HFO-1234ze) represented by $CF_3CH=CHF$;
3,3,3-trifluoropropene (HFO-1243ze) represented by $CF_3CH=CH_2$;
1,1,2,2,2-pentafluoroethane (HFC-125) represented by $CHF_2CF_3$;
difluoromethane (HFC-32) represented by $CF_2H_2$;
chlorodifluoromethane (HCFC-23) represented by $CHClF_2$;
etc.

Method for Separating 2,3,3,3-Tetrafluoropropene and Hydrogen Fluoride

Hereinbelow, the method of the present invention is specifically described based on FIG. 1, which shows a flow diagram of treatment steps in the case where a mixture comprising HFO-1234yf and HF is a treatment target.

(1) Liquid-Liquid Separation Step

According to the method shown in FIG. 1, first, a mixture comprising HFO-1234yf and HF is supplied to a separation tank A, and the mixture is cooled and separated into an upper liquid phase having a high concentration of HF and a lower liquid phase having a high concentration of HFO-1234yf.

The cooling temperature is not particularly limited. The HF concentration in the lower liquid phase can be lowered by reducing the cooling temperature.

FIG. 2 shows a liquid-liquid equilibrium curve of the mixture of HFO-1234yf and HF. In FIG. 2, the plot shows actual values and the solid line shows the results obtained by approximation using the NRTL equation based on the actual values. As can be clearly seen from FIG. 2, the cooling temperature is preferably as low as possible in order to separate the lower liquid phase having a high concentration of HFO-1234yf. Usually, a temperature of −5° C. or below, at which phase separation of HFO-1234yf and HF is observed, is preferable, with a temperature of −20° C. or below being more preferable. In addition, the lower the cooling temperature is, the shorter the relaxation time of phase separation is likely to be. Accordingly, liquid-liquid separation can be more efficiently performed when the cooling temperature is lower. However, when the cooling temperature is excessively lowered, the amount of energy required for cooling becomes large. Accordingly, in view of economic efficiency, the cooling temperature is preferably not lower than approximately −60° C. Cooling in the range described above allows a mixed liquid phase (lower liquid phase) of HFO-1234yf and HF in which the mole fraction of HF is in a range of about 0.09 to 0.25 to be obtained.

The HF-rich upper liquid phase obtained in this step can be taken out from the separation tank A and reused, for example, as a raw material in a step of fluorinating HCFO-1233xf to produce HFO-1234yf.

(2) Distillation Step

Next, the lower liquid phase obtained by the above method is fed to a distillation column B and distilled. HFO-1234yf and HF form a minimum azeotropic mixture. Further, when carrying out the present invention, usually, the liquid-liquid separation step is controlled so that the lower liquid phase contains a larger amount of HFO-1234yf than that of the minimum azeotropic mixture. Accordingly, in the distillation step, the mixture of HFO-1234yf and HF becomes a mixture having a boiling point lower than that of HFO-1234yf, and can be continuously withdrawn from the top of the column as an azeotropic or azeotrope-like mixture of HFO-1234yf and HF or a non-azeotropic mixture of HFO-1234yf and HF, depending on the distillation conditions.

The azeotropic or azeotrope-like mixture of HFO-1234yf and HF or the non-azeotropic mixture of HFO-1234yf and HF is continuously withdrawn from the top of the column by the above-described distillation operation, and thereby the HF concentration gradually decreases from the top toward the bottom of the column. Consequently, a substantially HF-free mixture can be obtained in the bottom of the column.

The term "azeotropic mixture" used herein refers to a mixture in which a vapor in equilibrium with a mixed liquid shows the same composition as the mixed liquid. The term "azeotrope-like mixture" used herein refers to a mixture in which a vapor in equilibrium with a mixed liquid shows a similar composition as the mixed liquid and in which the properties thereof are substantially the same as those of the azeotropic mixture.

FIG. 3 is a graph showing a gas-liquid equilibrium curve (x-y curve) of the mixture of HFO-1234yf and HF at 15° C. The graph shows examples of azeotropic, azeotrope-like, and non-azeotropic compositions of the mixture of HFO-1234yf and HF. This graph shows the results obtained by simulation using the Wilson method based on the measured actual values. Under atmospheric pressure, HFO-1234yf and HF become an azeotropic mixture with a ratio of HFO-1234yf:HF=95.4:4.6 (weight ratio), and become an azeotrope-like mixture with a ratio of HFO-1234yf:HF=92.2:7.8 to 99.3:0.7 (weight ratio). In the method of the present invention, substantially the same effects can be achieved both when the mixture of HFO-1234yf and HF has an azeotropic composition and when the same mixture has an azeotrope-like composition.

In the above-described distillation step, compared to the case where a non-azeotropic mixture is withdrawn from the top of the column, the case where an azeotropic or azeotrope-like mixture is withdrawn from the top of the column requires a withdrawal of a smaller amount HFO-1234yf to separate the same amount of HF, and thus allows substantially HF-free HFO-1234yf to be more efficiently obtained from the bottom of the column.

According to the method of the present invention, even when the mixture comprising HFO-1234yf and HF contains components other than HFO-1234yf and HF (hereinafter such components are sometimes referred to as "impurities"), HFO-1234yf can be purified by separating HFO-1234yf and HF by using the same method as described above. In this case, depending on the concentration of impurities and distillation treatment conditions, impurities are contained in the column top product or in the column bottom product in the distillation column.

In the case where the mixture comprising HFO-1234yf and HF contains impurities, particularly when the mixture contains an impurity having a boiling point between the boiling point of an azeotropic mixture of HFO-1234yf and HF and the boiling point of HFO-1234yf, withdrawal of a non-azeotropic mixture containing HFO-1234yf and HF from the top of the column in the distillation step allows such an impurity to be withdrawn simultaneously with the non-azeotropic mixture. Thus, high-purity HFO-1234yf can be easily obtained. Examples of impurities having a boiling point between the boiling point of the above-described azeotropic mixture and the boiling point of HFO-1234yf include trifluoroethane, 3,3,3-trifluoropropyne, etc.

The present invention, a mixture comprising HFO-1234yf as a main component obtained from the bottom of the column can be purified by, for example, conventional treatments such as distillation, liquid-liquid separation, extraction, extractive distillation, etc., and thereby obtaining a finished product.

FIG. 4 is a flow diagram showing treatment steps when the mixture of HFO-1234yf and HF as a treatment target contains HCFO-1233xf. In this case, in the separation tank A, the HFO-1234yf-rich lower liquid phase obtained by liquid-liquid separation contains HCFO-1233xf.

The lower liquid phase is fed to a distillation column B and distilled, and thereby a mixture containing HFO-1234yf and HF is continuously removed from the top of the column. HCFO-1233xf may be included in either or both of the column top product and the column bottom product, depending on the concentration thereof in the mixed solution and the operation conditions of the distillation column. FIG. 4 is a flow diagram of the case where HCFO-1233xf is included in both of the column top product and the column bottom product.

In regard to the mixture containing HFO-1234yf and HCFO-1233xf, which is obtained as the column bottom product, it is possible to purify HFO-1234yf by separating HCFO-1233xf by conventional distillation or extractive distillation. HCFO-1233xf obtained in this step can be reused, for example, as a raw material used for the fluorination reaction of HCFO-1233xf.

According to the present invention, in either case described above, a mixture having a small amount of HF obtained in the liquid-liquid separation step is used as a treatment target in the distillation step. Therefore, the amount of HF to be removed is small, and it is possible to reduce the operation load of the distillation column and relatively reduce the size of treatment equipment.

Further, the mixture containing HFO-1234yf and HF, which is obtained from the top of the column, can be reused as a treatment target of the present invention by, for example, feeding the mixture to the separation tank A again and using the same as a part of raw materials for the liquid-liquid separation treatment.

Advantageous Effects of Invention

According to the method of the present invention, HF and HFO-1234yf contained in a mixture containing HF and HFO-1234yf can be separated under simple and economically advantageous conditions.

DESCRIPTION OF EMBODIMENTS

Hereinafter, the present invention is described in detail with reference to Examples.

Example 1

Figure 1:
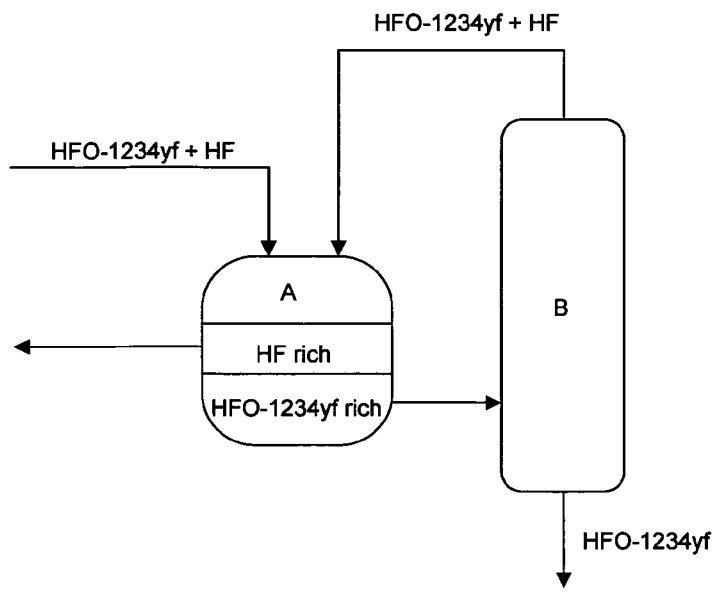
FIG. 1 is a flow diagram showing an example of the present invention when a mixture of HFO-1234yf and HF is a treatment target.
Figure 2:
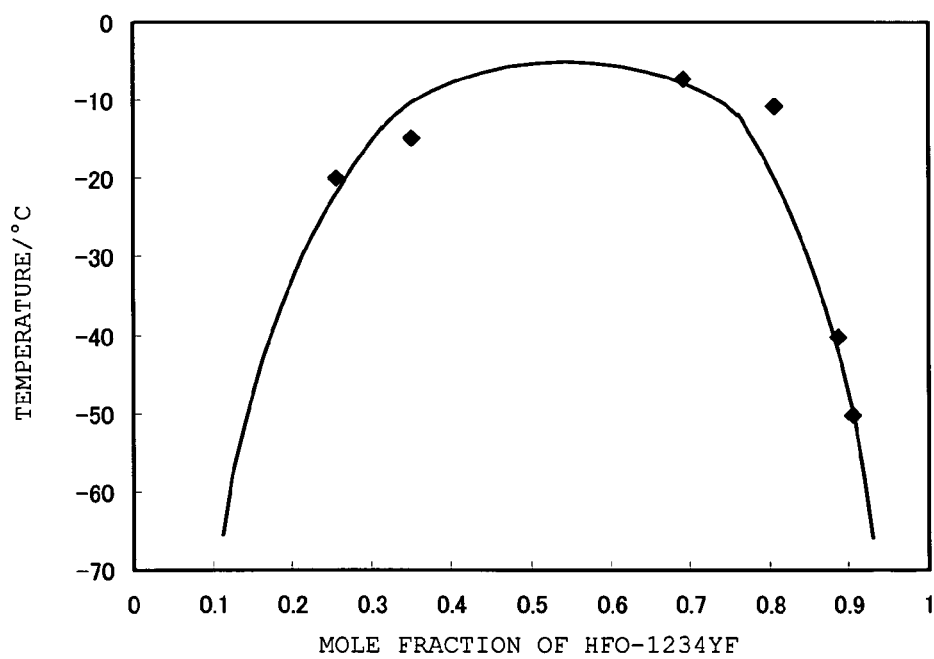
FIG. 2 is a liquid-liquid equilibrium curve of a mixture of HFO-1234yf and HF.
Figure 3:
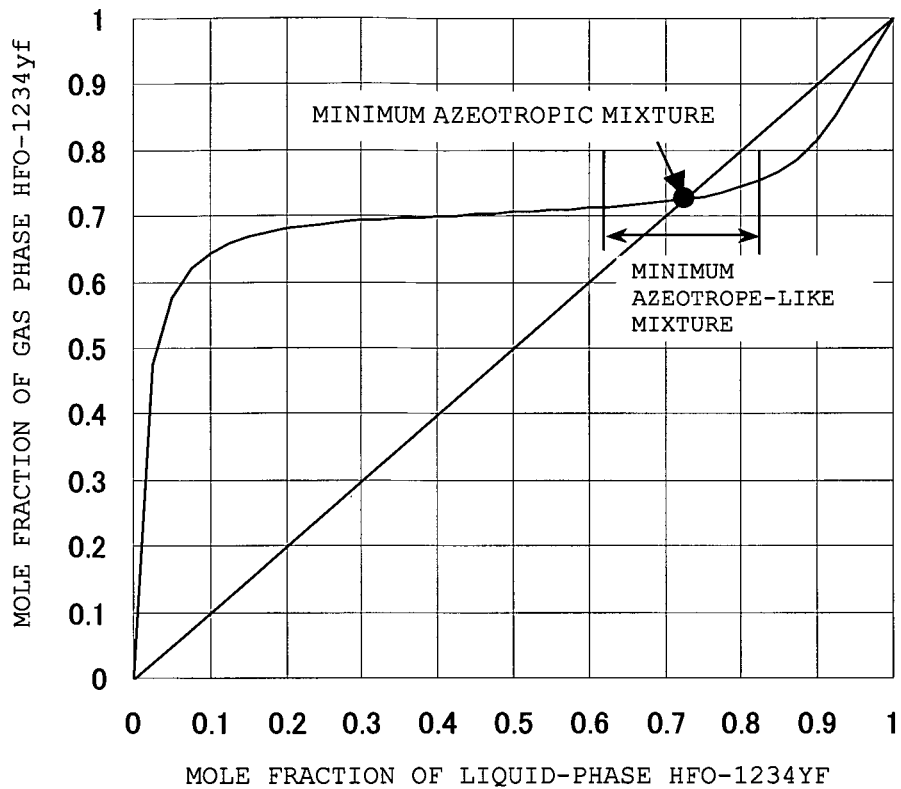
FIG. 3 is a gas-liquid equilibrium curve (x-y curve) of a mixture of HFO-1234yf and HF at 15° C.
Figure 4:
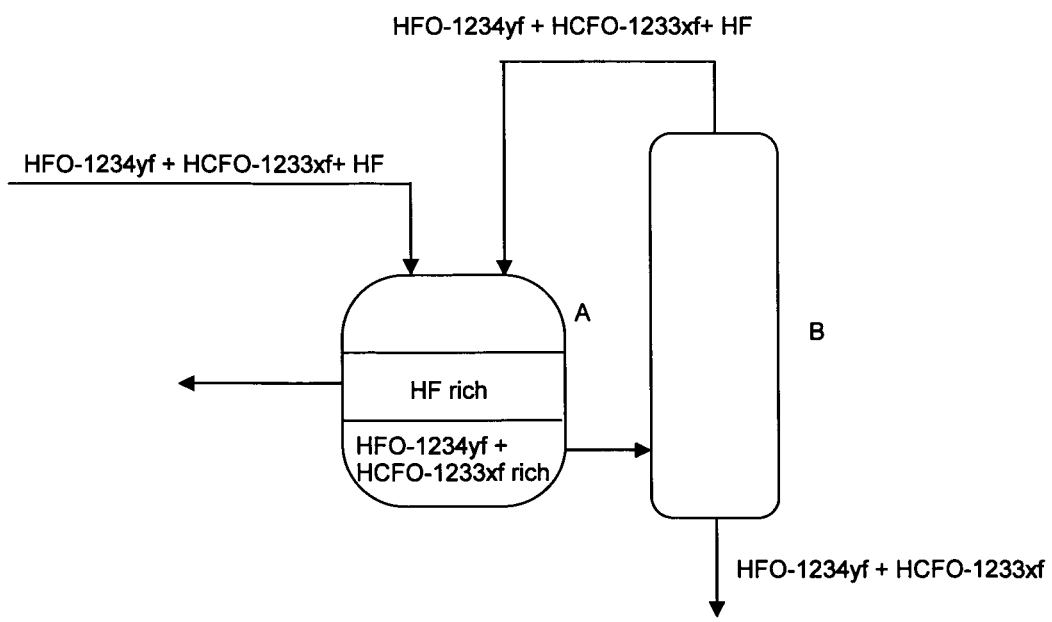
FIG. 4 is a flow diagram showing an example of the present invention when a mixture comprising HFO-1234yf, HCFO-1233xf, and HF is a treatment target.
Figure 5:
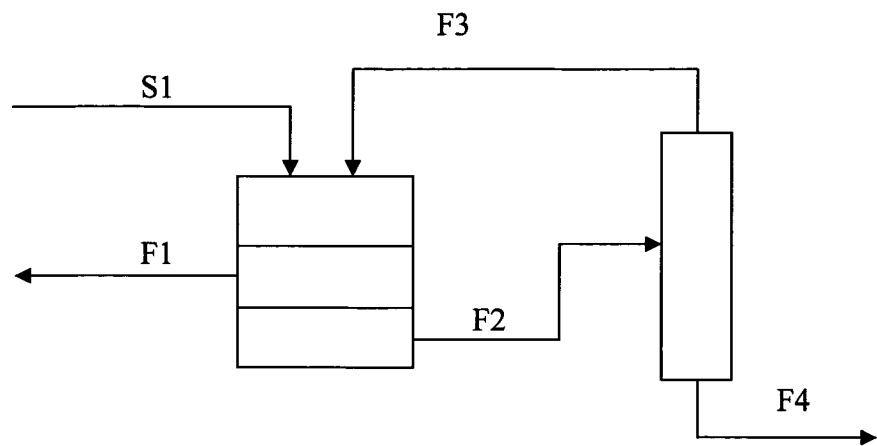
FIG. 5 is a flow diagram showing treatment steps of a mixture of HFO-1234yf and HF in Example 1.

HF was separated from a mixture containing HFO-1234yf and HF by the method described below. This method is described based on the flow diagram shown in FIG. 5.

A mixed gas (S1) of HFO-1234yf and HF shown in Table 1 below was first condensed, and then introduced to a separation tank. In the separation tank, the liquid mixture was cooled to −40° C., and separated into Fraction 1 (F1) containing HF as a main component and Fraction 2 (F2) containing HFO-1234yf as a main component.

Fraction 2 (F2) was fed to a distillation column and distilled (column top temperature: 28° C., pressure: 0.7 MPaG), and the remaining HF was removed. A mixture of HF and HFO-1234yf was withdrawn from the top of the column and recycled as Fraction 3 (F3) back into the separation tank. Then, Fraction 4 (F4) that does not substantially contain HF was obtained from the bottom of the column, and fed to the next step.

Table 1 shows the composition of the product in each step described above.

The above process enables separation of HF from HFO-1234yf without employing a method used in conventional techniques that uses highly corrosive sulfuric acid.

TABLE 1

| Mass Flow kg/hr | S1 | F1 | F2 | F3 | F4 |
|---|---|---|---|---|---|
| HF | 1.53 | 1.53 | 0.92 | 0.92 | 0.00 |
| 1234yf | 15.74 | 1.16 | 69.99 | 55.40 | 14.59 |

Example 2

Figure 6:
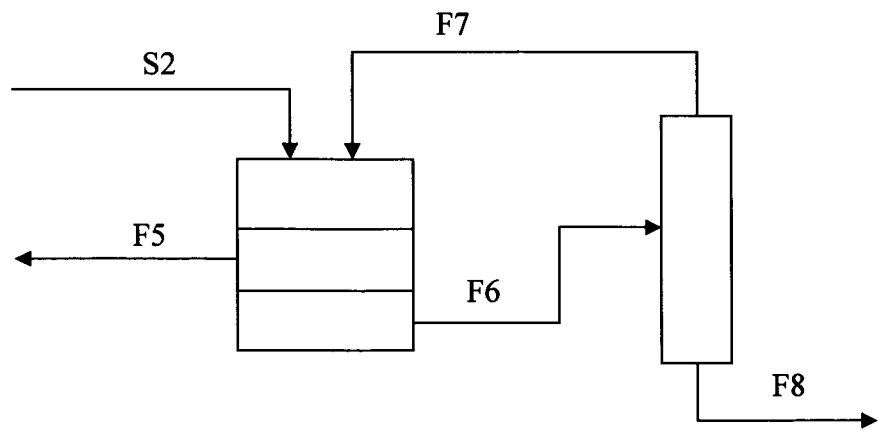
FIG. 6 is a flow diagram showing treatment steps of a mixture of HFO-1234yf and HF in Example 2.

HF was separated from a mixture containing HFO-1234yf and HF by the method described below. This method is described based on the flow diagram shown in FIG. 6.

A mixed gas (S2) of HFO-1234yf and HF shown in Table 2 below was first condensed, and then introduced to a separation tank, cooled to −40° C., and separated into Fraction 5 (F5) containing HF as a main component and Fraction 6 (F6) containing HFO-1234yf as a main component.

Fraction 6 (F6) was fed to the distillation column and distilled (column top temperature: 28° C., pressure: 0.7 MPaG), and the remaining HF was removed. In the distillation step, the mixture of HF and HFO-1234yf was withdrawn from the top of the column as an azeotrope-like composition, and recycled as Fraction 7 (F7) back into the separation tank. Then, Fraction 8 (F8) that does not substantially contain HF was withdrawn from the bottom of the column, and fed to the next step.

The above process enables separation of HF from HFO-1234yf without employing a method used in conventional techniques that uses highly corrosive sulfuric acid.

TABLE 2

| Mass Flow kg/hr | S2 | F5 | F6 | F7 | F8 |
|---|---|---|---|---|---|
| HF | 1.53 | 1.53 | 0.25 | 0.25 | 0.00 |
| 1234yf | 15.74 | 1.14 | 18.23 | 3.62 | 14.61 |

Example 3

Figure 7:
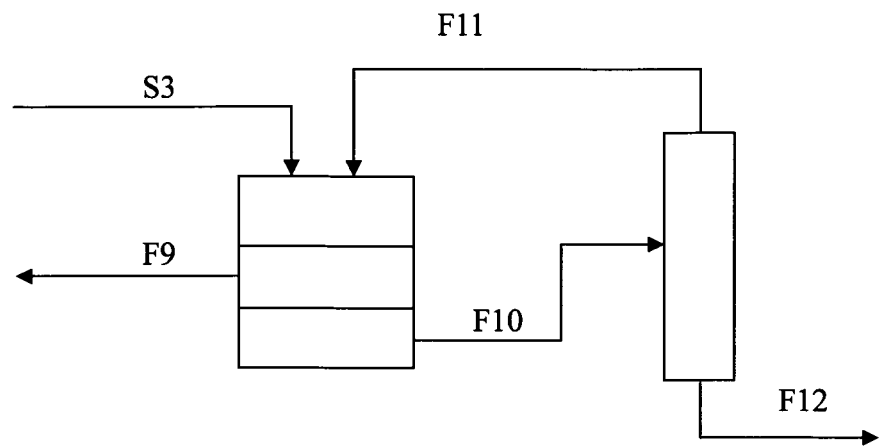
FIG. 7 is a flow diagram showing treatment steps of a mixture containing HCFO-1233xf, HFO-1234yf, and HF in Example 3.

HF was separated from a mixture containing HCFO-1233xf, HFO-1234yf, and HF by the method described below. This method is described based on the flow diagram shown in FIG. 7.

First, a mixed gas (S3) of HCFO-1233xf, HFO-1234yf, and HF shown in Table 3 below was condensed into a liquid mixture, and this liquid mixture was introduced to a separation tank. In the separation tank, the liquid mixture was cooled to −40° C. and was thereby separated into two phases, i.e., an upper liquid phase (F9) comprising HF as a main component and a lower liquid phase (F10) comprising HCFO-1233xf and HFO-1234yf as main components.

The lower liquid phase (F10) was fed to a distillation column and distilled (column top temperature: 28° C., pressure: 0.7 MPaG). Thereby, a column top product containing HFO-1234yf and HF was withdrawn and recycled back into the separation tank. Then, a column bottom product that does not substantially contain HF was withdrawn from the bottom of the column and fed to the next step.

Table 3 shows the composition of the product in each step described above.

TABLE 3

| Mass Flow kg/hr | S3 | F9 | F10 | F11 | F12 |
|---|---|---|---|---|---|
| HF | 1.95 | 1.95 | 1.16 | 1.16 | 0.00 |
| 1234yf | 15.60 | 1.33 | 85.17 | 70.91 | 14.26 |
| 1233xf | 1.78 | 0.01 | 1.77 | 0.00 | 1.77 |

Example 4

Figure 8:
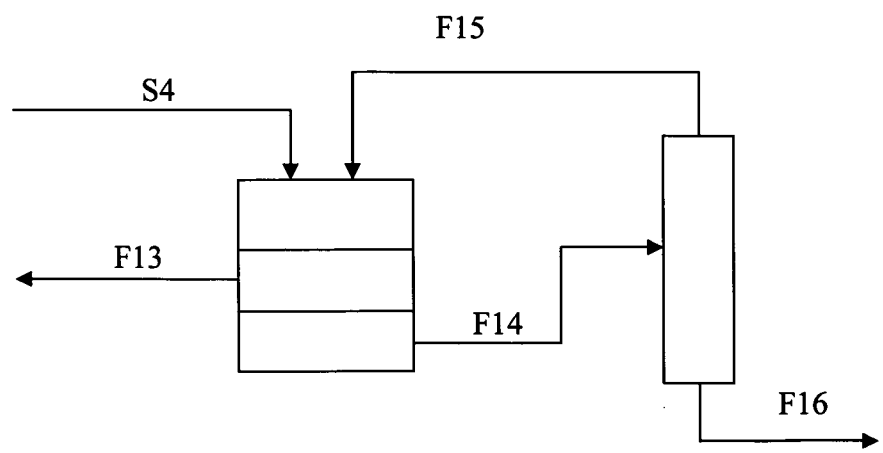
FIG. 8 is a flow diagram showing treatment steps of a mixture containing HCFO-1233xf, HFO-1234yf, and HF in Example 4.

HF was separated from a mixture containing HCFO-1233xf, HFO-1234yf, and HF by the method described below. This method is described based on the flow diagram shown in FIG. 8.

First, a mixed gas comprising HFCO-1233xf, HFO-1234yf, and HF shown in Table 4 below was condensed, introduced to a separation tank (S4), cooled to −40° C., and separated into Fraction 13 (F13) comprising HF as a main component and Fraction 14 (F14) comprising HFCO-1233xf and HFO-1234yf as main components.

Fraction 14 (F14) was fed to the distillation column and distilled (column top temperature: 28° C., pressure: 0.7 MPaG), and the remaining HF was removed. In the distillation step, the mixture of HF and HFO-1234yf was withdrawn from the top of the column as an azeotrope-like composition, and recycled as Fraction 15 (F15) back into the separation tank. Then, Fraction 16 (F16) that does not substantially contain HF was withdrawn from the bottom of the column, and fed to the next step.

Table 4 shows the composition of the product in each step described above.

The above process enables separation of HF from HFO-1234yf and HFO-1233xf, without employing a method used in conventional techniques that uses highly corrosive sulfuric acid.

TABLE 4

| Mass Flow kg/hr | S4 | F13 | F14 | F15 | F16 |
|---|---|---|---|---|---|
| HF | 1.95 | 1.95 | 0.30 | 0.30 | 0.00 |
| 1234yf | 15.60 | 1.00 | 19.02 | 4.42 | 14.60 |
| 1233xf | 1.78 | 0.04 | 1.74 | 0.00 | 1.74 |

As can be clearly seen from Tables 3 and 4 above, according to the methods in Examples 3 and 4, a substantially HF-free mixture of HCFO-1233xf and HFO-1234yf was obtained from the bottom of the distillation column by subjecting the mixed solution containing HCFO-1233xf, HFO-1234yf, and HF to the liquid-liquid separation treatment and the distillation treatment. The mixture containing HFCO-1233xf and HFO-1234yf, which was obtained by the above method, can be easily separated into HCFO-1233xf and HFO-1234yf by a method such as distillation.

The above method enables separation of each component from the mixture containing HFO-1234yf, HCFO-1233xf, and HF, without employing a method used in conventional techniques that uses highly corrosive sulfuric acid.

COMPARATIVE EXAMPLE 1

Figure 9:
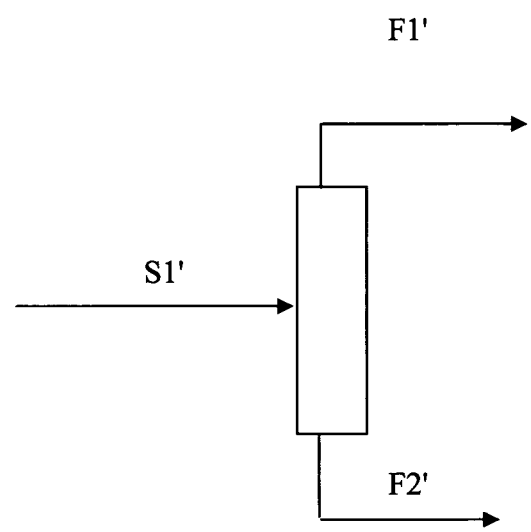
FIG. 9 is a flow diagram showing treatment steps of a mixture containing HCFO-1233xf, HFO-1234yf, and HF in Comparative Example 1.

According to the flow diagram shown in FIG. 9, a liquid mixture (S1') containing HCFO-1233xf, HFO-1234yf, and HF was distilled (column top temperature: 28° C., pressure: 0.7 MPaG) without being subjected to liquid-liquid separation, and was separated into a column top product (F1') and a column bottom product (F2'). Table 5 shows the composition of the products in the above step.

TABLE 5

| | S1' | F1' | F2' |
|---|---|---|---|
| HF | 1.95 | 1.17 | 0.77 |
| 1234YF | 15.60 | 15.44 | 0.16 |
| 1233XF | 1.78 | 0.00 | 1.78 |

As can be clearly seen from Table 5, in regard to the liquid mixture containing HCFO-1233xf, HFO-1234yf, and HF, it was not possible to completely remove HF from HFO-1234yf by simply directly distilling the mixture.

The invention claimed is:

1. A method for purifying 2,3,3,3-tetrafluoropropene comprising the steps of:
   (1) cooling a liquid mixture containing 2,3,3,3-tetrafluoropropene and hydrogen fluoride to separate the liquid mixture into an upper liquid phase having a high hydrogen fluoride concentration and a lower liquid phase having a high 2,3,3,3-tetrafluoropropene concentration, wherein the temperature to cool the liquid mixture containing 2,3,3,3-tetrafluoropropene and hydrogen fluoride in step (1) is −5° C. or below; and
   (2) subjecting the lower liquid phase obtained in step (1) to a distillation operation and withdrawing a mixture containing 2,3,3,3-tetrafluoropropene and hydrogen fluoride from a top of a distillation column, thereby obtaining 2,3,3,3-tetrafluoropropene that does not substantially contain hydrogen fluoride from a bottom of the distillation column.

2. The method according to claim 1, wherein the mixture containing 2,3,3,3-tetrafluoropropene and hydrogen fluoride withdrawn from the top of the distillation column in step (2) is an azeotropic or azeotrope-like mixture.

3. The method according to claim 1, wherein the mixture containing 2,3,3,3-tetrafluoropropene and hydrogen fluoride withdrawn from the top of the distillation column in step (2) is a non-azeotropic mixture.

4. The method according to claim 1, wherein cooling in step (1) is performed on the liquid mixture containing 2,3,3,3-tetrafluoropropene and hydrogen fluoride to which the mixture containing 2,3,3,3-tetrafluoropropene and hydrogen fluoride withdrawn from the top of the distillation column is added.

5. The method according to claim 1, wherein the liquid mixture containing 2,3,3,3-tetrafluoropropene and hydrogen fluoride to be cooled in step (1) further contains 2-chloro-3,3,3-trifluoropropene.

6. The method for purifying 2,3,3,3-tetrafluoropropene according to claim 5 further comprising a step of subjecting the column bottom product obtained in step (2) to a distillation operation to remove 2-chloro-3,3,3-trifluoropropene.

7. The method according to claim 2, wherein cooling in step (1) is performed on the liquid mixture containing 2,3,3,3-tetrafluoropropene and hydrogen fluoride to which the mixture containing 2,3,3,3-tetrafluoropropene and hydrogen fluoride withdrawn from the top of the distillation column is added.

8. The method according to claim 3, wherein cooling in step (1) is performed on the liquid mixture containing 2,3,3,3-tetrafluoropropene and hydrogen fluoride to which the mixture containing 2,3,3,3-tetrafluoropropene and hydrogen fluoride withdrawn from the top of the distillation column is added.

9. The method according to claim 2, wherein the liquid mixture containing 2,3,3,3-tetrafluoropropene and hydrogen fluoride to be cooled in step (1) further contains 2-chloro-3,3,3-trifluoropropene.

10. The method according to claim 3, wherein the liquid mixture containing 2,3,3,3-tetrafluoropropene and hydrogen fluoride to be cooled in step (1) further contains 2-chloro-3,3,3-trifluoropropene.

11. The method according to claim 4, wherein the liquid mixture containing 2,3,3,3-tetrafluoropropene and hydrogen fluoride to be cooled in step (1) further contains 2-chloro-3,3,3-trifluoropropene.

12. The method for purifying 2,3,3,3-tetrafluoropropene according to claim 9 further comprising a step of subjecting the column bottom product obtained in step (2) to a distillation operation to remove 2-chloro-3,3,3-trifluoropropene.

13. The method for purifying 2,3,3,3-tetrafluoropropene according to claim 10 further comprising a step of subjecting the column bottom product obtained in step (2) to a distillation operation to remove 2-chloro-3,3,3-trifluoropropene.

14. The method for purifying 2,3,3,3-tetrafluoropropene according to claim 11 further comprising a step of subjecting the column bottom product obtained in step (2) to a distillation operation to remove 2-chloro-3,3,3-trifluoropropene.

* * * * *